United States Patent
Wysocki et al.

(10) Patent No.: US 10,053,791 B2
(45) Date of Patent: Aug. 21, 2018

(54) METHOD FOR OBTAINING A COMPOSITE COATING ON TITANIUM IMPLANTS FOR TISSUE ENGINEERING

(71) Applicants: Jackson State University, Jackson, MS (US); Warsaw University Of Technology, Warsaw (PL)

(72) Inventors: Bartlomiej Wysocki, Warsaw (PL); Danuta Leszczynska, Jackson, MS (US); Wojciech Swieszkowski, Warsaw (PL); Krzysztof Jan Kurzydlowski, Warsaw (PL)

(73) Assignee: JACKSON STATE UNIVERSITY, Jackson, MS (US)

(*) Notice: Subject to any disclaimer, the term of this patent is extended or adjusted under 35 U.S.C. 154(b) by 0 days.

(21) Appl. No.: 14/866,785

(22) Filed: Sep. 25, 2015

(65) Prior Publication Data

US 2017/0088969 A1 Mar. 30, 2017

(51) Int. Cl.
| | |
|---|---|
| *A61L 27/30* | (2006.01) |
| *A61L 27/32* | (2006.01) |
| *A61L 27/50* | (2006.01) |
| *A61L 27/06* | (2006.01) |
| *C25D 15/00* | (2006.01) |
| *C25D 9/08* | (2006.01) |
| *C25D 7/00* | (2006.01) |

(52) U.S. Cl.
CPC .............. *C25D 15/00* (2013.01); *A61L 27/06* (2013.01); *A61L 27/303* (2013.01); *A61L 27/32* (2013.01); *A61L 27/50* (2013.01); *C25D 7/00* (2013.01); *C25D 9/08* (2013.01); *A61L 2400/12* (2013.01); *A61L 2400/18* (2013.01); *A61L 2420/04* (2013.01); *A61L 2420/06* (2013.01); *A61L 2430/02* (2013.01)

(58) Field of Classification Search
None
See application file for complete search history.

(56) References Cited

U.S. PATENT DOCUMENTS

| | | | |
|---|---|---|---|
| 6,183,255 B1* | 2/2001 | Oshida | A61C 8/0012 433/201.1 |
| 2003/0176927 A1* | 9/2003 | Steinemann | A61F 2/30767 623/23.55 |
| 2015/0125952 A1* | 5/2015 | Kim | A61L 27/14 435/366 |

OTHER PUBLICATIONS

Kaya et al., "Carbon Nanotube-Reinforced Hydroxyapatite Coatings on Metallic Implants Using Electrophoretic Deposition," Key Engineering Materials, available Online: Jun. 15, 2009, vol. 412, pp. 93-97.*

Dlugon et al., "Spectroscopic studies of electrophoretically deposited hybrid HAp/CNT coatings on titanium," Spectrochimica Acta Part A: Molecular and Biomolecular Spectroscopy, 133 (2014) 872-875.*

* cited by examiner

*Primary Examiner* — Aradhana Sasan
(74) *Attorney, Agent, or Firm* — Butler Snow LLP

(57) ABSTRACT

A composite coating and method for preparing the composite coating on titanium implants for tissue culture and tissue engineering is provided. The implants are characterized in that the titanium component to be coated is placed in a aqueous solution containing calcium cations, phosphate anions, and dispersed carbon nanoparticles (such as single layer graphene oxide or graphene oxide) in an amount of about 0.05%-1.50% by weight relative to the total weight of aqueous solution. The dimensions of the dispersed graphene oxide should be around, but not limited to, 300-800 nm (X-Y), while their thickness is about 0.7-1.2 nm. The aqueous solution with carbon nanoparticles is prepared by mixing for at least 72 h in temperature in range 20-35° C. and sonicated before electrodeposition process. In the prepared solution is further placed titanium which acts as cathode element (may be the implant), and anode which can be, for example, a platinum rod. Between the cathode and anode is set a potential from −1.3V to −1.7V which results in coating formation by electrodeposition. The titanium implant before the electrodeposition process is treated in sodium hydroxide of HF to improve coating formation and thickness.

21 Claims, No Drawings

METHOD FOR OBTAINING A COMPOSITE COATING ON TITANIUM IMPLANTS FOR TISSUE ENGINEERING

FIELD OF THE INVENTION

The aim of the invention is a method of fabrication of composite coating on titanium implants for tissue engineering.

BACKGROUND OF THE INVENTION

Titanium and its alloys are widely used in medicine as implants because of their biocompatibility and corrosion resistance. Furthermore, titanium alloys are good for the load-bearing applications because of high strength to weight ratio, high fatigue resistance, and relatively low, as for metals, Young's modulus. In addition, the Young's modulus and the associated stiffness of implant can by controlled by increasing porosity. There are many publications in which the positive impact of high roughness and porosity of the implant on the emergence of a strong connection between it and the bone is shown. The pore sizes of 100-400 microns is considered most preferred for biological implants, as it favors the penetration of the cells, tissue growth, vascularization, and nutrient transport.

The viability of titanium in the human body is determined to be around 20 years, but it could be extended up to twice, where the most common modification of the surface is with calcium-phosphate coating fabrication directly on titanium alloys. The calcium-phosphates coating on an implant provides a barrier, shielding tissues from possible release of ions from the titanium and other alloys. Furthermore, all calcium-phosphate ceramics are a good substrate as a structural support for cells, and cells proliferation. The most common calcium-phosphate ceramic used for implants is hydroxyapatite with chemical formula $Ca_{10}(PO_4)_6(OH_2)$. Hydroxyapatite is the major inorganic mineral component of human bone, and numerous publications show that hydroxyapatite ceramic coating is the best promoter of proliferation of implanted cells, increases their survival, and improves their metabolism, when compared to the uncoated implant.

The biggest disadvantage of calcium-phosphate ceramics produced by engineering method is their low mechanical strength, which is revealed by the tendency to cracking and falling off of the implant shell fragments. The biggest disadvantage of the popular methods for producing hydroxyapatite coating on implants by thermal spraying is unfeasibility to use those methods when the entire volume of the porous implant has to be covered evenly.

SUMMARY OF THE INVENTION

The aim of the invention is to provide a biocompatible, bioactive, and mechanically resistant to peeling coating uniformly covering the entire surface of the porous implant. Furthermore, it is appropriate to obtain a mechanical strength increase compared to a ceramic coating with high porosity coverage having favorable adhesion and proliferation. A secondary aim of the invention is to obtain bactericidal properties, good reproducibility of process, and the low cost of the method.

The invention relates to a composite coating and a method for preparing the composite coating on titanium implants into tissue culture comprising hydroxyapatite and carbon nanoparticles (e.g., graphene oxide or single layer graphene oxide) on a solid titanium implant and porous scaffolds made of titanium for tissue culture and tissue engineering. In some embodiments the solid implant and porous scaffolds are made of titanium alloys.

The method according to the invention is that the coated titanium component is placed in an aqueous solution containing calcium cations, phosphate anions (V) and dispersed in a solution of graphene oxide flakes. While this aqueous electrolytic solution comprises calcium cations, phosphate anions, and dispersed graphene oxide, it preferably consists essentially of calcium cations, phosphate anions, and dispersed graphene oxide, where contaminants are contemplated to possibly be introduced through, for example, one or more of the reagent components, aqueous solution, or acidic/basic solutions used to align the pH of the aqueous solution. Purity of the reagents is most preferred. Afterwards the titanium component is connected to the source of −1.3-−1.7V electric voltage in system where it acts as a cathode. The anode in this system is, for example, a platinum rod while calomel electrode is a reference. The amount of graphene oxide is 0.05%-1.5% by weight relative to the total weight amount of the aqueous solution. The graphene oxide used had one or more lattices, while its size was around 300-800 nm (X-Y) and a thickness 0.7-1.2 nm. The aqueous solution before electrodeposition process is mixed at a temperature in the range of 20° C.-35° C. and exposed to ultrasonic waves. The surface of the titanium element before electrodeposition process is activated by etching with sodium hydroxide. In the case of components made by methods of rapid prototyping is also possible by etching with hydrofluoric acid.

The amount of added graphene oxide is calculated from the formula:

$$mGO[g] = m_r[g] \cdot \% \, GO$$

where:
mGO [g]—mass of graphene oxide used to produce the coating in grams;
$m_r$[g]—mass of aqueous solution of calcium and phosphate ions, expressed in grams; and
% GO—graphene oxide to be added to the aqueous solution expressed in a percentage.

Hydrated or unhydrated calcium nitrate $Ca(NO_3)_2$ is preferably used as a source of calcium ions, and hydrated or unhydrated potassium phosphate $K_2HPO_4$ is preferably used as a source of phosphate ions.

DETAILED DESCRIPTION

The following detailed description is presented to enable any person skilled in the art to make and use the invention. For purposes of explanation, specific details are set forth to provide a thorough understanding of the present invention. However, it will be apparent to one skilled in the art that these specific details are not required to practice the invention. Descriptions of specific applications are provided only as representative examples. Various modifications to the preferred embodiments will be readily apparent to one skilled in the art, and the general principles defined herein may be applied to other embodiments and applications without departing from the scope of the invention. The present invention is not intended to be limited to the embodiments shown, but is to be accorded the widest possible scope consistent with the principles and features disclosed herein.

The aim of the invention is to provide a biocompatible, bioactive, and mechanically resistant to peeling coating uniformly covering the entire surface of the porous implant. Furthermore, it is appropriate to obtain a mechanical strength increase compared to a ceramic coating with high porosity coverage having favorable adhesion and proliferation. A secondary aim of the invention is to obtain bactericidal properties, good reproducibility of process, and the low cost of the method.

The invention relates to a method for preparing a composite coating on titanium implants into tissue culture comprising hydroxyapatite and (e.g., graphene oxide or single layer graphene oxide) on a solid titanium implant and porous scaffolds made of titanium for tissue culture and tissue engineering. In some embodiments the solid implant and porous scaffolds are made of titanium alloys.

The method according to the invention is that the coated titanium component is placed in an aqueous solution containing calcium cations, phosphate anions (V) and dispersed in a solution of graphene oxide flakes. While this aqueous electrolytic solution comprises calcium cations, phosphate anions, and dispersed graphene oxide, it preferably consists essentially of calcium cations, phosphate anions, and dispersed graphene oxide, where contaminants are contemplated to possibly be introduced through, for example, one or more of the reagent components, aqueous solution, or acidic/basic solutions used to align the pH of the aqueous solution. Purity of the reagents is most preferred. Afterwards the titanium component is connected to the source of −1.3-- 1.7V electric voltage in system where it acts as a cathode. The anode in this system is, for example, a platinum rod while calomel electrode is a reference. The amount of graphene oxide is 0.05%-1.5% by weight relative to the total weight amount of the aqueous solution. The graphene oxide used had one or more lattices, while its size was around 300-800 nm (X-Y) and a thickness 0.7-1.2 nm. The aqueous solution before electrodeposition process is mixed at a temperature in the range of 20° C.-35° C. and exposed to ultrasonic waves. The surface of the titanium element before electrodeposition process is activated by etching with sodium hydroxide. In the case of components made by methods of rapid prototyping is also possible by etching with hydrofluoric acid.

The amount of added graphene oxide is calculated from the formula:

$$mGO[g] = m_r[g] \cdot \% \, GO$$

where:
mGO [g]—mass of graphene oxide used to produce the coating in grams;
$m_r$[g]—mass of aqueous solution of calcium and phosphate ions, expressed in grams; and
% GO—graphene oxide to be added to the aqueous solution expressed in a percentage.

Hydrated or unhydrated calcium nitrate $Ca(NO_3)_2$ is preferably used as a source of calcium ions, and hydrated or unhydrated potassium phosphate $K_2HPO_4$ is preferably used as a source of phosphate ions.

The disclosed method can be used for the production of composite coating containing hydroxyapatite and graphene on any titanium element, also porous with complicated shapes and small micrometric pores. The obtained composite hydroxyapatite+graphene coating is characterized by high mechanical strength because of graphene nanoparticles, which inhibits the propagation of cracks. In contrast to the method where coating strengthen by carbon nanomaterials is fabricated by electrophoresis, the disclosed method of the invention allows the formation of hydroxyapatite from solution containing $Ca^{2+}$ and $PO_4^{3-}$ ions. Fabrication of calcium-phosphates by electrodeposition from a solution of ions exclude inter alia the need of buying expensive commercial hydroxyapatite granulate, and enable control of the atomic ratio of calcium and phosphorous in the produced coating. Obtained by electrodeposition, the coating has a more uniform morphology and is fabricated throughout the entire volume of the porous implant. Manufacturing process of fabrication coatings from commercial hydroxyapatite requires the use of ceramic powders much smaller than the size of pores, which in tissue engineering should not exceed 400 microns for the pores. Fabrication of calcium-phosphate coatings by electrodeposition from a solution of ions does not limit the pore size of an implant.

The fabrication of the coating processed correctly in our tests, the current was constantly decreasing during coating electrodeposition, which suggested continuous increase of the coating thickness over time. A good coverage was observed on metallic implants of various shapes and varying porosity ranges, and good adhesion to the surface of the implants. The hydroxyapatite-graphene composite coating test results and characterization has shown the following:

10-160% increase in the thickness of the calcium-phosphate coating in contrast to an electrodeposition process without graphene oxide;

the calcium-phosphate coating increase was dependent on the amount of graphene-oxide dissolved in aqueous solution and the process time;

a quantity limit of graphene oxide that is possible to use in solution was related to diffusion of ions within the structure, and the graphene oxide limit was set to be around 1.5% by weight of the solution;

a higher morphological homogeneity was achieved throughout the whole implant volume when compared to other fabrication methods;

a higher mechanical strength was achieved when compared to coatings made without graphene oxide;

a higher surface development promoting cell proliferation and differentiation was achieved; and the electrodeposition solution was positively confirmed for its bactericidal properties.

FORMULA EXAMPLES

Formula I mass percent of graphene oxide: 0.05% by weight $Ca(NO_3)_2 \cdot 4H_2O$:2.48 g/L $K_2HPO_4 \cdot 3H_2O$:1.90 g/L electric voltage between cathode (titanium) and anode (platinum): −1.4V
time of electrodeposition: 60 minutes
coating thickness: 2 [μm]

Formula II mass percent of graphene oxide: 0.05% by weight $Ca(NO_3)_2 \cdot 4H_2O$:9.91 g/L $K_2HPO_4 \cdot 3H_2O$:1.90 g/L electric voltage between cathode (titanium) and anode (platinum): −1.4V
time of electrodeposition: 60 minutes
coating thickness: 2 [μm]

Formula III mass percent of graphene oxide: 0.75% by weight $Ca(NO_3)_2 \cdot 4H_2O$:2.48 g/L K$_2$HPO$_4$.3H$_2$O:1.90 g/L electric voltage between cathode (titanium) and anode (platinum): −1.4V
time of electrodeposition: 60 minutes
coating thickness: 5.1 [μm]

Formula IV mass percent of graphene oxide: 0.75% by weight

Ca(NO$_3$)$_2$.4H$_2$O:9.91 g/L

K$_2$HPO$_4$.3H$_2$O:7.590 g/L electric voltage between cathode (titanium) and anode (platinum): −1.4V
time of electrodeposition: 60 minutes
coating thickness: 5.2 [μm]

Formula V mass percent of graphene oxide: 1.5% by weight

Ca(NO$_3$)$_2$.4H$_2$O:2.48 g/L

K$_2$HPO$_4$.3H$_2$O:1.90 g/L electric voltage between cathode (titanium) and anode (platinum): −1.4V
time of electrodeposition: 60 minutes
coating thickness: 2.5 [μm]

Formula VI mass percent of graphene oxide: 1.5% by weight

Ca(NO$_3$)$_2$.4H$_2$O:9.91 g/L

K$_2$HPO$_4$.3H$_2$O:7.59 g/L electric voltage between cathode (titanium) and anode (platinum): −1.4V
time of electrodeposition: 60 minutes
coating thickness: 2.5 [μm]

Reagents employed for the fabrication of the composite hydroxyapatite-graphene coating were: calcium cations and phosphate anions (V) dissociated in water, and well-dispersible graphene. The reagents used in electrodeposition were Ca(NO$_3$)$_2$/Ca(NO$_3$)$_2$.4H$_2$O and K$_2$HPO$_4$/K$_2$HPO$_4$.3H$_2$O (i.e., hydrates or anhydrates), and Graphene Oxide (GO), or Single Layer Graphene Oxide(SLGO). Electrodeposition solution containing calcium nitrate and potassium phosphate was prepared in a glass beaker and stirred for 1 hour with cover. The solution pH was set in range 4.5-5.2, while deviations from this value were aligned by concentrated hydrochloric acid (HCl) or sodium hydroxide (NaOH). Afterwards, the GO or SLGO was added to solution, which was further stirred for 72 hours with temperature ranging 20° C.-35° C. for promoting dispersion of nanoparticles for electrodeposition. To ensure appropriate dispersion of carbon nanoparticles in solution, 1 hour of sonication was performed before the coating process.

The prepared solution acts as an electrolyte during electrodeposition in the system where working electrode (cathode) is titanium, and the anode is a platinum wire. The surface of the titanium element before electrodeposition process is activated by treating with sodium hydroxide. In the case of components made by rapid prototyping methods, it is also recommended that the surfaces are pre-processed by etching in hydrofluoric acid. During current flow in a potentiostatic mode between −1.3V and −1.7V, the electrodeposition process is followed on the cathode by a process of calcium ions reduction and oxidation of phosphorous ions which result in a calcium-phosphate with Ca—P ratio from (1.5-1.67) formation. Furthermore because of graphene nanoparticles dispersion in solution, the formed coating is a resulting hydroxyapatite-graphene composite.

Graphene Oxide (GO) and Single Layer Graphene Oxide (SLGO) has attached to their surfaces carboxyl, expoxy, and hydroxyl groups, which enhance their reactivity with other compounds. Graphene used in the fabrication process was obtained by company CheapTubes.com (112 Mercury Drive, Brattleboro, Vt. 05301 USA) in the modified Hummers process. The Hummers method is a chemical method for fabrication of graphene from graphite in redox reaction using potassium permanganate (KMnO$_4$) and sulfuric acid (H$_2$SO$_4$). Graphene oxide fabricated in these method reaches 300-800 nm dimensions in the XY plane and a thickness of 0.7-1.2 nm.

On the basis of the total weight of the aqueous solution containing a mixture of calcium nitrate and potassium phosphate necessary for the full immersion of the titanium element, the calculated mass of graphene oxide was determined and added. The percentage of graphene oxide in solution was between the range of about 0.05% and about 1.5% by weight of the electrolytic solution. These values were established through set of experiments. The mass of graphene oxide was calculated as follows based on solutions of calcium and phosphate ions for electrodeposition:

1. 4.96 g/L-9.91 g/L Ca(NO$_3$)$_2$.4H$_2$O and 3.80 g/L-7.59 g/L K$_2$HPO$_4$.3H$_2$O;

2. 2.48 g/L-9.91 g/L Ca(NO$_3$)$_2$.4H$_2$O and 2.20 g/L-4.40 g/L K$_2$HPO$_4$;

3. 2.39 g/L-4.79 g/L Ca(NO$_3$)$_2$ and 3.80 g/L-7.59 g/L K$_2$HPO$_4$.3H$_2$O;

4. 2.39 g/L-4.79 g/L Ca(NO$_3$)$_2$ and 2.20 g/L-4.40 g/L K$_2$HPO$_4$.

Values were determined in experimental studies. The mass of the graphene oxide used in solution was calculated from the formula:

$$mGO[g] = m_r[g] \cdot \% \, GO$$

where:
mGO [g]—mass of graphene oxide used to produce the coating in grams;
$m_r$[g]—mass of aqueous solution of calcium and phosphate ions, expressed in grams; and
% GO—graphene oxide to be added to the aqueous solution expressed in a percentage.

Fabricated coatings were subjected to basic quality control involving visual inspection, scanning electron microscope morphology inspection, optical profilometry, X-ray phase composition studies, energy dispersive X-ray calcium and phosphorous atomic ratio studies. In addition, scaffold porosity test by μ-CT (computerized X-ray microtomography) were performed and bactericidal tests on electrolyte solution (bioluminescence). The resulting coatings were characterized by a uniform coating with high porosity over the entire volume of the implant. No spatter cover fragments prove the high adhesion of the coating and mechanical properties increase in comparison to methods like soaking in Simulated Body Fluid (SBF). The resulting coatings were thicker than coatings fabricated without addition of graphene oxide, up to 160%. The resulting composite coating on titanium implants meets the requirements for testing in vitro and in vivo, which is necessary for the implant to be on the market.

Basic research on the fabricated composite coatings has shown:
  The presence of a biocompatible hydroxyapatite complex: the chemical formula $Ca_{10-x}(HPO_4)_x(PO_4)_6\text{-}x(OH)_{2-x}$ (0<x<1) and the chemical formula $Ca_{10}(PO_4)_6(OH)_2$,
  Highly developed surface of the composite coating which is around 2.0-5.2 μm thick,
  The lamellar structure of highly porous coating which mimics natural bone, and should improve cell response,
  Coherent coverage of the entire volume of the porous implant having contact with electrolytic solution,
  No coating delamination providing for well-chosen process parameters and implementation in the composite coating of the graphene nanoparticles which annihilate crack propagation, and
  Bactericidal properties of electrolytic solution for deposition were confirmed. A well-known toxicity bioassay with use of bacteria *Vibrio fischeri* was performed to assess potential toxicity of electrolyte solution (bioluminescence test).

The terms "comprising," "including," and "having," as used in the claims and specification herein, shall be considered as indicating an open group that may include other elements not specified. The terms "a," "an," and the singular forms of words shall be taken to include the plural form of the same words, such that the terms mean that one or more of something is provided. The term "one" or "single" may be used to indicate that one and only one of something is intended. Similarly, other specific integer values, such as "two," may be used when a specific number of things is intended. The terms "preferably," "preferred," "prefer," "optionally," "may," and similar terms are used to indicate that an item, condition or step being referred to is an optional (not required) feature of the invention.

The invention has been described with reference to various specific and preferred embodiments and techniques. However, it should be understood that many variations and modifications may be made while remaining within the spirit and scope of the invention. It will be apparent to one of ordinary skill in the art that methods, devices, device elements, materials, procedures and techniques other than those specifically described herein can be applied to the practice of the invention as broadly disclosed herein without resort to undue experimentation. All art-known functional equivalents of methods, devices, device elements, materials, procedures and techniques described herein are intended to be encompassed by this invention. Whenever a range is disclosed, all subranges and individual values are intended to be encompassed. This invention is not to be limited by the embodiments disclosed, including any shown in the drawings or exemplified in the specification, which are given by way of example and not of limitation.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

All references throughout this application, for example patent documents including issued or granted patents or equivalents, patent application publications, and non-patent literature documents or other source material, are hereby incorporated by reference herein in their entireties, as though individually incorporated by reference, to the extent each reference is at least partially not inconsistent with the disclosure in the present application (for example, a reference that is partially inconsistent is incorporated by reference except for the partially inconsistent portion of the reference).

We claim:

1. A method for preparing a composite coating on an implant comprising:
  providing an aqueous electrolytic solution, wherein the aqueous electrolytic solution comprises calcium cations, phosphate anions, and dispersed graphene oxide nanoparticles;
  placing the implant into the aqueous electrolytic solution; and
  applying a voltage between a cathode and anode for electrodeposition of the calcium cations, phosphate anions, and dispersed graphene oxide nanoparticles onto the implant.

2. The method of claim 1, further comprising etching the implant prior to the step of placing the implant into the aqueous electrolytic solution.

3. The method of claim 2, wherein the etching is performed by treating the implant with sodium hydroxide.

4. The method of claim 2, wherein the etching is performed by treating the implant with hydrofluoric acid.

5. The method of claim 1, wherein the implant is comprised of titanium.

6. The method of claim 1, wherein the implant is comprised of an alloy of titanium.

7. The method of claim 1, wherein the aqueous electrolytic solution is prepared by mixing the calcium cations, phosphate anions, and dispersed graphene oxide nanoparticles for at least 72 hours at temperature in a range of about 20° C. to about 35° C. and the aqueous electrolytic solution is sonicated prior to electrodeposition.

8. The method of claim 1, further comprising reversibly connecting the cathode element in electrical connection with the implant and placing the anode in electrical connection with the aqueous electrolytic solution.

9. The method of claim 1, wherein the voltage applied between the cathode and anode is set to a potential from −1.3V to −1.7V for electrodeposition.

10. The method of claim 1, wherein an amount of the dispersed graphene oxide nanoparticles included in the aqueous electrolytic solution is between 0.05% and 1.5% by total weight of the aqueous electrolytic solution and is calculated by:

$$m\text{GO}[g] = m_r[g] \cdot \% \text{ GO}$$

where:
  mGO [g]=mass of the dispersed graphene oxide nanoparticles included set in grams,
  $m_r$[g]=mass of the aqueous electrolytic solution of the calcium cations and phosphate anions set in grams, and
  % GO=the dispersed graphene oxide nanoparticles addition to the aqueous electrolytic solution set in percentage.

11. A method for preparing a composite coating on a titanium implant for tissue engineering comprising:
  providing an aqueous electrolytic solution, wherein the aqueous electrolytic solution consists essentially of calcium cations, phosphate anions, and dispersed graphene oxide nanoparticles;
  placing the titanium implant into the aqueous electrolytic solution;

physically attaching a cathode element to the titanium implant and providing an anode element in electrical connection with the aqueous electrolytic solution, wherein the anode comprises platinum; and applying a voltage between the cathode and the anode for electrodeposition of the calcium cations, phosphate anions, and dispersed graphene oxide nanoparticles onto the titanium implant.

12. The method of claim 11, wherein the calcium cations are provided by dissolved hydrated or unhydrated calcium nitrate.

13. The method of claim 11, wherein the phosphate anions are phosphate anions (V) and are provided by dissolved hydrated or unhydrated potassium phosphate.

14. The method of claim 11, further comprising etching the titanium implant prior to the step of placing the titanium implant into the aqueous electrolytic solution.

15. The method of claim 14, wherein the etching is performed by treating the titanium implant with sodium hydroxide.

16. The method of claim 14, wherein the etching is performed by treating the titanium implant with hydrofluoric acid.

17. The method of claim 11, wherein the titanium implant is comprised of an alloy of titanium.

18. The method of claim 11, wherein the dispersed graphene oxide nanoparticles has dimensions in a range of about 300-800 nm and a thickness of around 0.7-1.2 nm.

19. The method of claim 11, wherein an amount of the dispersed graphene oxide nanoparticles included in the aqueous electrolytic solution is between about 0.05% and 1.5% by total weight of the aqueous electrolytic solution and is calculated by:

$$mGO[g] = m_r[g] \cdot \% \, GO$$

mGO [g]=mass of the dispersed graphene oxide nanoparticles included set in grams, $m_r$[g]=mass of the aqueous electrolytic solution of the calcium cations and phosphate anions set in grams, and % GO=the dispersed graphene oxide nanoparticles addition to the aqueous electrolytic solution set in percentage.

20. An implant with a composite coating comprising hydroxyapatite and graphene oxide nanoparticles wherein the implant is coated with the composite coating by placing the implant into the aqueous electrolytic solution comprising calcium cations, phosphate anions, and dispersed graphene oxide nanoparticles and wherein the implant is subjected to electrodeposition of the calcium cations, phosphate anions, and dispersed graphene oxide nanoparticles.

21. The implant with a composite coating of claim 20, wherein an amount of the dispersed graphene oxide nanoparticles included in the aqueous electrolytic solution is between about 0.05% and 1.5% by total weight of the aqueous electrolytic solution and is calculated by:

$$mGO[g] = m_r[g] \cdot \% \, GO$$

where:

mGO [g]=mass of the dispersed graphene oxide nanoparticles included set in grams, $m_r$[g]=mass of the aqueous electrolytic solution of the calcium cations and phosphate anions set in grams, and % GO=the dispersed graphene oxide nanoparticles addition to the aqueous electrolytic solution set in percentage.

* * * * *